United States Patent
Neumann (10) Patent No.: US 10,207,038 B2
(45) Date of Patent: Feb. 19, 2019

(54) PUMP FOR IMPLANTATION INTO A VESSEL

(71) Applicant: UNIVERSITAET DUISBURG-ESSEN, Essen (DE)

(72) Inventor: Till Neumann, Bochum (DE)

(73) Assignee: UNIVERSITAT DUISBURG-ESSEN (DE)

( * ) Notice: Subject to any disclaimer, the term of this patent is extended or adjusted under 35 U.S.C. 154(b) by 0 days.

(21) Appl. No.: 15/317,763

(22) PCT Filed: Jun. 10, 2015

(86) PCT No.: PCT/EP2015/062919
§ 371 (c)(1),
(2) Date: Dec. 9, 2016

(87) PCT Pub. No.: WO2015/189259
PCT Pub. Date: Dec. 17, 2015

(65) Prior Publication Data
US 2017/0119945 A1    May 4, 2017

(30) Foreign Application Priority Data

Jun. 12, 2014  (DE) .................. 10 2014 211 216

(51) Int. Cl.
*A61M 1/10* (2006.01)
*A61M 1/12* (2006.01)

(52) U.S. Cl.
CPC ........ *A61M 1/1031* (2014.02); *A61M 1/1024* (2014.02); *A61M 1/1032* (2014.02);
(Continued)

(58) Field of Classification Search
None
See application file for complete search history.

(56) References Cited

U.S. PATENT DOCUMENTS 4,964,864 A * 10/1990 Summers .............. F04C 13/001
                                                        600/16
5,965,089 A * 10/1999 Jarvik .................. A61M 1/101
                                                        422/44
(Continued)

FOREIGN PATENT DOCUMENTS

WO    WO 2015/052303 A1    4/2015

OTHER PUBLICATIONS

International Search Report and Written Opinion prepared by the European Patent Office dated Aug. 18, 2015, for International Application No. PCT/EP2015/062919.

*Primary Examiner* — Catherine Voorhees
*Assistant Examiner* — Elizabeth K So
(74) *Attorney, Agent, or Firm* — Sheridan Ross P.C.

(57) ABSTRACT

The disclosure relates to a pump for implantation into a vessel or a heart, with the pump being introduced in a first state into the vessel or heart in order then be functionally changed over to a second state in the vessel or in the heart, having
    a drive part and
    a delivery part,
    where the drive part is not functional in the first state and becomes functional as a result of the changeover to the second state, wherein the drive part has an electric motor, where the electric motor is embodied as a wet rotor, and where, in the first state, the rotor of the electric motor and the stator of the electric motor are arranged so as to be separate from one another, and where the rotor of the electric motor is moved into the stator of the electric motor in the second state, where the rotor can drive the delivery part in the second state.

21 Claims, 7 Drawing Sheets

(52) U.S. Cl.
CPC ........ *A61M 1/1036* (2014.02); *A61M 1/1086* (2013.01); *A61M 1/125* (2014.02); *A61M 2205/0266* (2013.01); *A61M 2205/8243* (2013.01)

(56) References Cited

U.S. PATENT DOCUMENTS

| | | | |
|---|---|---|---|
| 8,641,594 B2* | 2/2014 | LaRose | A61M 1/101 600/16 |
| 8,690,749 B1 | 4/2014 | Nunez | |
| 9,138,518 B2* | 9/2015 | Campbell | A61M 1/101 |
| 9,358,329 B2* | 6/2016 | Fitzgerald | A61M 1/1008 |
| 2006/0122456 A1* | 6/2006 | LaRose | A61M 1/1017 600/16 |
| 2009/0093764 A1* | 4/2009 | Pfeffer | A61M 1/1031 604/151 |
| 2011/0004046 A1* | 1/2011 | Campbell | A61M 1/101 600/16 |
| 2011/0275884 A1* | 11/2011 | Scheckel | F04D 29/247 600/16 |
| 2013/0138205 A1 | 5/2013 | Kushwaha et al. | |
| 2014/0051908 A1 | 2/2014 | Khanal et al. | |
| 2015/0141739 A1* | 5/2015 | Hsu | A61M 1/1036 600/16 |

* cited by examiner

PUMP FOR IMPLANTATION INTO A VESSEL

CROSS REFERENCE TO RELATED APPLICATIONS

This application is a national stage application under 35 U.S.C. 371 and claims the benefit of PCT Application No. PCT/EP2015062919 having an international filing date of 10 Jun. 2015, which designated the United States, which PCT application claimed the benefit of German Patent Application No. 10 2014 211 216.8 filed 12 Jun. 2014, the disclosure of each of which are incorporated herein by reference.

BACKGROUND

Cardiac insufficiency is one of the most prevalent internal-medicine diseases in the developed countries of this world. An increased frequency of cardiac insufficiency is observed with increasing age.

In general, cardiac insufficiency is understood as the inability of the heart to supply the organism with sufficient blood circulation. It should also be noted that reduced blood circulation (also referred to as reduced cardiac output) results in an insufficient supply of oxygen and/or nutrients to the tissue. This can manifest itself symptomatically in reduced physical capacity and/or increased shortness of breath (so-called dyspnea), as well as increased water retention (e.g., edema in the legs). The causes of this will not be addressed further here.

Furthermore, it should be noted that cardiac insufficiency is also frequently associated with a dilated left ventricle with reduced pumping function.

Since populations are becoming increasingly older, an increasing number of sick people can also be expected. This means an increasing need for treatment.

Previous approaches to treatment are oriented towards the respective stage of the disease.

In the so-called mild and moderate stages (New York Heart Association NYHA I-II), treatment is generally administered in the form of medication. In addition, there is the possibility of implanting a defibrillator (implantable cardioverter-defibrillator (ICD)) or cardiac resynchronization therapy (CRT).

In the advanced and terminal stages (New York Heart Association NYHA III-IV), a heart transplantation must be considered in some circumstances. Alternatively, particularly in elderly patients, the use of a left ventricular assist device (LVAD) is also indicated. Since the number of donor organs is limited, the use of a left ventricular assist device can also be used as an interim measure.

Previous LVAD systems consisted of contacting/pulsing units which due to their size, for example were arranged partially outside of the body. Newer LVAD systems are generally placed intracorporeally and have a continuous flow. A delivery rate of up to 8 liters per minute can be made available with the newer systems, thus enabling the entire cardiac output to be replaced.

However, the various newer LVAD systems are nonetheless disadvantageous for a wide variety of reasons that will be outlined below.

One thing that all of these systems have in common is that they must be implanted by means of an operation. As a rule, this entails opening up the thorax, and the support of a cardiopulmonary machine is often required. In other words, a costly and risk intervention under general anesthesia is necessary. What is more, all of these newer systems have an external power unit and/or an external control unit. The connection of the external systems is critical, since the danger exists of germs penetrating along the wired connection. Furthermore, the previous newer systems are designed for continuous support, so a high level of blood flow is maintained even in periods in which there is no elevated need, such as during resting periods. This generally has a negative impact on the size of the required power supply unit and thus poses an obstacle to the shift to an intracorporeal design. Moreover, use of the previous systems in patients with peripheral occlusive arterial disease (POAD) and so-called porcelain aorta (calcified aorta) is very restricted.

BRIEF DESCRIPTION OF THE INVENTION

It is the object of the invention to provide an improved pump that resolves one or more of the drawbacks of the prior art.

The object is achieved by a pump for implantation into a vessel or a heart, with the pump being introduced in a first state into the vessel or heart in order to then be functionally changed over to a second state in the vessel or in the heart. The pump has a drive part and a delivery part, with the delivery part having a drive shaft, the drive part being non-functional in the first state and becoming functional owing to the changeover to the second state, the drive part having an electric motor, the electric motor being embodied as a wet rotor, and the rotor of the electric motor being arranged separately from the stator of the electric motor in the first state so that a rotation of the rotor (R) by the stator (S) is not possible, and the rotor of the electric motor being moved into the stator of the electric motor in the second state, with the rotor being able to drive the delivery part in the second state.

BRIEF DESCRIPTION OF THE FIGURES

The invention is explained in further detail below with reference to the enclosed figures.

DETAILED DESCRIPTION

According to the present invention, a pump 1 for implantation in a vessel or a heart is proposed. Although it can be used in different vascular systems, reference will be made below only to the implantation thereof into the heart or the cardiac muscle or a heart vessel without thereby limiting the generality of the invention.

The design of the pump 1 according to the invention enables implantation by means of a so-called minimally invasive technique. For example, the pump 1 can be mounted on a guide wire and advanced using conventional catheter technique to the application site or pushed only via a guide wire and fastened there and deployed. Other techniques for placement at the application site are not excluded by this, however, but rather are readily apparent to a person skilled in the art. For example, the pump 1 according to the invention also allows for placement by means of a catheter or a sheath.

To this end, the pump 1 is embodied according to the invention such that it can produce the required pump output and yet be small enough that it can be transported through an appropriate vessel (lumen) to the application site without damaging this vessel.

In addition, the design of the pump 1 enables the pump 1 to be introduced apically or atrially into a patient's heart.

This is very advantageous particularly in the case of calcified vessels, e.g., a porcelain aorta.

Figure 1A:
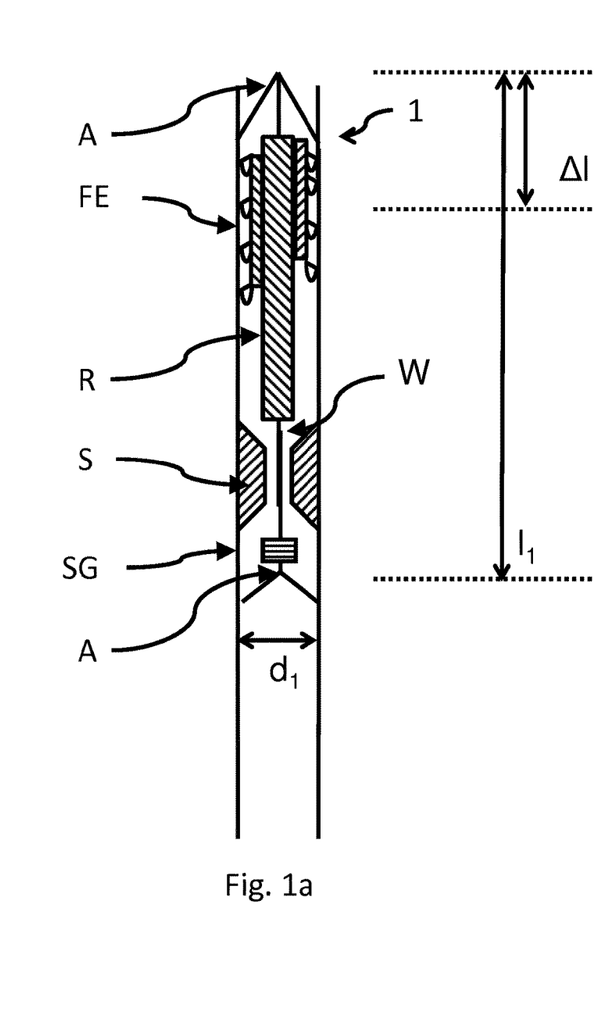
FIG. 1a shows an exemplary schematic, axial, sectional representation of a principle of the inventive pump in a first state.
Figure 1B:
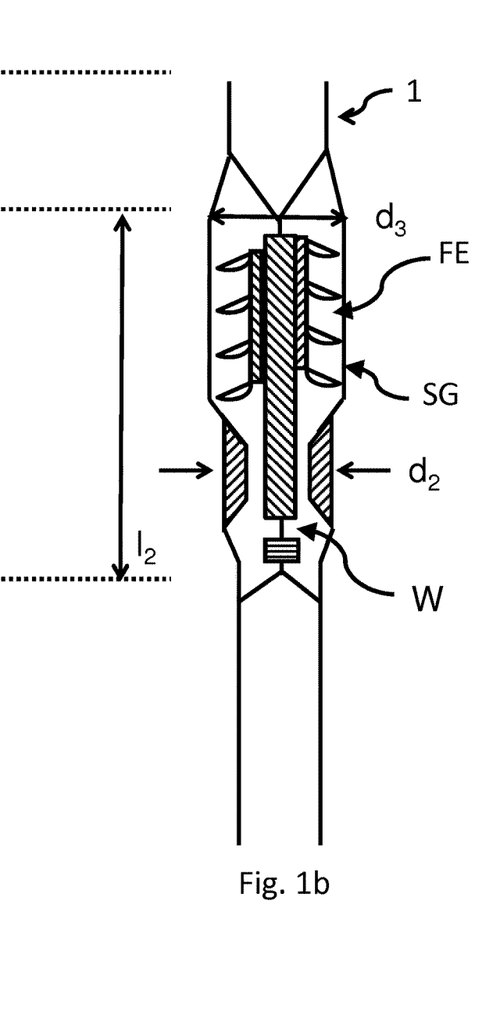
FIG. 1b shows an exemplary schematic, axial, sectional representation of a principle of the inventive pump in a second state.

FIGS. 1a and 1b illustrate a basic principle of the invention.

What is shown is an exemplary schematic representation of a principle of the pump according to the invention in a first state for delivery to the application site (FIG. 1a) and in a second state ready for operation at the application site, each in an axial sectional representation.

A pump 1 for implantation into a vessel or a heart is first introduced into the body at an appropriate place. In the process, the pump 1 is in a first state, which is shown in FIG. 1a, in order to then be able to be functionally changed over to a second state in the vessel or in the heart.

For the purpose of being transported to the application site, the pump 1 is mounted in its first state on a wire guide of a suitable catheter, for example, or pushed via a guide wire. The pump 1 itself has a drive part and a delivery part FE. In the first state (FIG. 1a), the drive part is not yet functional. Particularly, the rotor (R) is still arranged so as to be spatially separated from the stator (S). In FIG. 1a, for example, the rotor is arranged spatially in front of the stator, and the stator is still shown in a collapsed state. The drive part only becomes functional as a result of being changed over to the second state. In FIGS. 1a and 1b, the delivery part is connected via a drive shaft W to the drive shaft.

The drive part has an electric motor, which is embodied as a wet rotor, for example. Wet rotors are especially advantageous, since they enable a comparably good flow rate while also not having any problems with respect to the fact that the motor must be specially encapsulated in order to prevent the motor from becoming gummed up or blocked or corroded by blood or components thereof and not posing a danger for the blood circulation by exchanging lubricants with the blood.

As a rule, the rotor R of the electric motor is arranged separately from the stator S of the electric motor for the transport.

In FIG. 1a, the stator S and the rotor R are still spatially separated, so the motor is not operable. Only through the introduction of the shaft do the stator S and the rotor R engage in one another, whereby the rotor R becomes rotatable in the stator S, upon which the delivery part FE can be caused to rotate (FIG. 1b).

The engagement can be brought about through a shortening of the shaft, or through a pushing-in or displacement. The shaft can be easily shortened by pulling a wire (e.g., via a catheter). Different techniques can be used for this purpose. Some examples of techniques include pulling or pushing exerted by means of a guide wire on a catheter, or by means of shape memory alloys or through spring forces, etc. For instance, the pump can be biased in the first state in the manner of a spring, and upon release of a locking mechanism or of a shape-retaining casing (e.g., sheath or catheter), the stored force is released and results in an expansion or to the assembly of the individual parts.

In the second state, which occurs at the application site, the rotor R can then drive the delivery part FE, particularly via a mechanical connection, generally a drive shaft W. The state is shown, for example, in FIG. 1b.

The shortening of the shaft W is indicated in the drawings for the sake of example. Particularly in FIGS. 1a and 1b, it is readily apparent that the length $l_1$ in the first state is changed over to a length $l_2$, where $l_1 > L_2$. That is, the shaft is shortened by $\Delta l$ during the transition into the second state.

Depending on the embodiment, the diameter $d_1$ in the region of the stator S in the second state can be widened slightly into a diameter $d_2$. What is more, the region of the delivery unit can be widened to a diameter $d_3$. Although $d_3 > d_2$ is shown in the figure, this need not necessarily be the case; rather, this is only intended for purposes of illustration in order to show that different regions can be widened differently in the operable second state. As a rule, the diameter $d_1$ in the first state is selected such that an application with a catheter having a diameter of 32 French or less, particularly 24 French or less, is possible. The widening of the diameters can occur simultaneously or successively.

Figure 2:
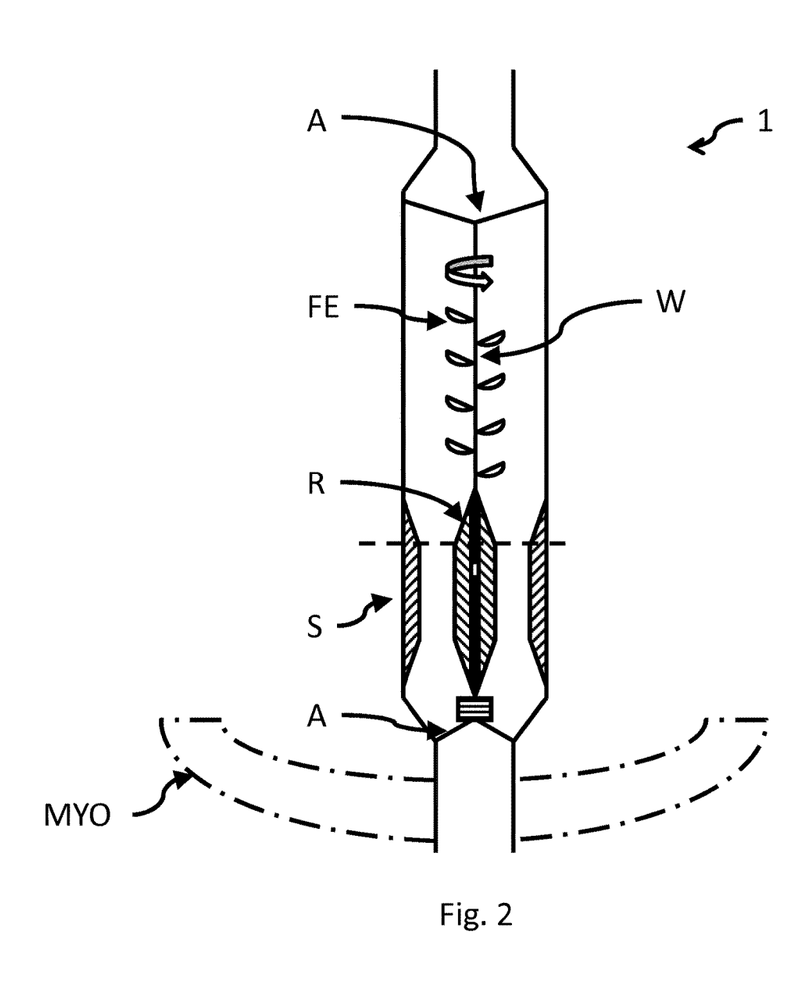
FIG. 2 shows an exemplary schematic arrangement of another embodiment of an inventive pump in a second state in the myocardium.

As indicated previously, the finished pump 1 can be anchored directly in or on a vessel or in the heart. For instance, FIG. 2 shows the anchoring in the cardiac muscle (myocardium) MYO within the heart according to one possible embodiment of the invention. Without limiting the generality, another application site can of course also be provided depending on the use of the pump 1 according to the invention.

Figure 3A:
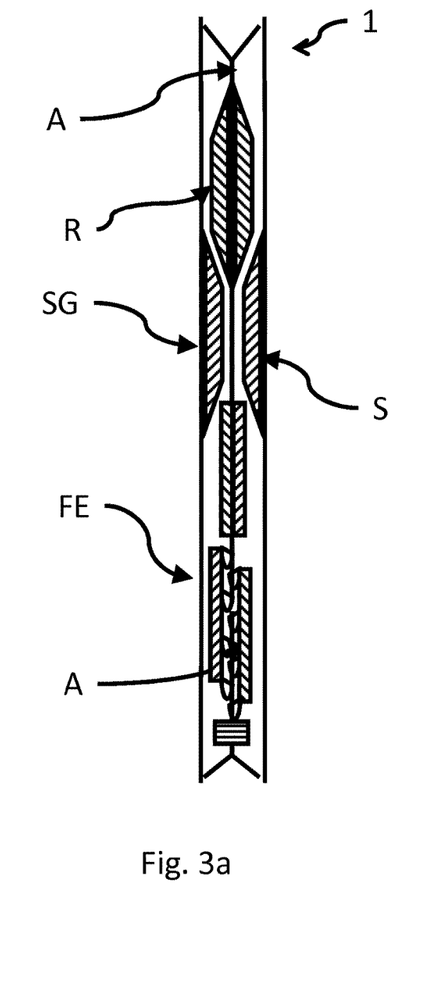
FIG. 3a shows an axial, sectional representation of an exemplary schematic arrangement of another embodiment of an inventive pump in a first state.
Figure 3B:
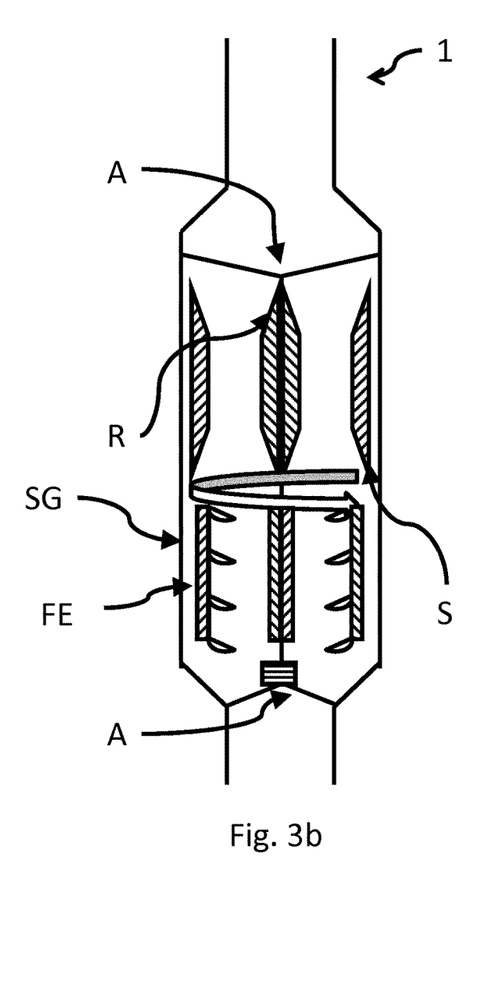
FIG. 3b shows an axial, sectional representation of an exemplary schematic arrangement of another embodiment of an inventive pump according to FIG. 3a in a second state.

FIGS. 3a and 3b show an axial cross section of another exemplary design of the pump 1 in a first state, which is shown in FIG. 3a, for placement in the application site and in a second state, which is shown in FIG. 3b, ready for operation at the application site. A radial cross section yields similar views, so a corresponding description will be omitted here.

A pump 1 for implantation into a vessel or a heart is then introduced into the cardiovascular system of the body at an appropriate place. In this process, the pump 1 is in a first state, which is shown in FIG. 3a, in order to then be able to be functionally changed over to a second state in the vessel or in the heart.

For the purpose of being transported to the application site, the pump 1 is mounted in its first state on a wire guide of a suitable catheter, for example, or pushed via a guide wire. Alternatively, the transport can also occur via a catheter or a sheath without a guide wire. The pump 1 itself has a drive part and a delivery part FE. In the first state (FIG. 3a), the drive part is not yet functional. The drive part only becomes functional as a result of being changed over to the second state. The delivery part FE is arranged here on an expandable segments [sic] that are driven by the (magnetically coupled) rotor R. For this purpose, the pump 1 also has a supporting structure SG, so that the delivery part FE does not rub against the wall of the vessel or heart. Different types of drive can be used. For instance, a magnetic bearing and coupling can be provided, or the bearing can be purely mechanical, or it can be magnetic and mechanical.

The drive part has an electric motor, which is embodied as a wet rotor, for example. Wet rotors are especially advantageous, since they enable a comparably good flow rate while also not having any problems with respect to the fact that the motor must be specially encapsulated in order to prevent the motor from becoming gummed up or blocked or corroded by blood or components thereof and not posing a danger for the blood circulation by exchanging lubricants with the blood.

As a rule, the rotor R of the electric motor is arranged separately from the stator S of the electric motor for the transport.

In FIG. 3a, the stator S and the rotor R are arranged initially in the first state one behind the other, i.e., on different planes, and the motor is not operable. The rotor R only becomes rotatable through the expansion in the region of the stator S and can then cause the delivery part FE to rotate (FIG. 3b).

The rotor R of the electric motor is only introduced into the stator S of the electric motor in the second state at the application site. Different techniques can be used for this purpose. Exemplary techniques include pulling or pushing exerted by means of a guide wire on a catheter or by means of shape memory alloys, or through spring forces, etc. For instance, the pump can be biased in the first state in the manner of a spring, and upon release (of a locking mechanism), the stored force is released and results in an expansion or to the assembly of the individual parts. As in FIG. 3b in comparison to FIG. 3a, an outer supporting structure SG can be deployed in the process. For instance, the expansion of the sleeve-like supporting structure SG can also be used to assemble the drive part so as to render it operable, for example by means of a shortening shaft. Besides widening the lumen in order to make pump output available, this expansion can also assume the function of supporting the pump 1 in the vessel or in the heart.

In the second state, which occurs at the application site, the rotor R can then drive the delivery part FE via the drive shaft W. The state is shown in FIG. 3b.

In the embodiment of FIGS. 3a and 3b, the delivery part FE is coupled magnetically to the drive part. This enables the delivery part FE to also be structured such that it takes up a very small cross section in the first state. In the first state, for example, the delivery part FE is arranged in two portions lying one behind the other. In the second state, the first portion of the delivery part is pushed or pulled into the second portion, for example through self-expansion or other suitable manipulations. Alternatively, the delivery unit FE can be connected directly to the drive unit via a common shaft.

Figure 4A:
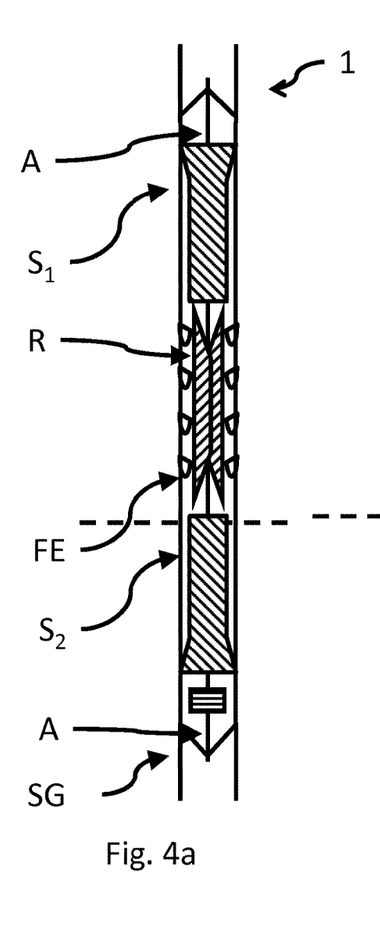
FIG. 4a shows an axial, sectional representation of an exemplary schematic arrangement of another embodiment of an inventive pump in a first state.
Figure 4B:
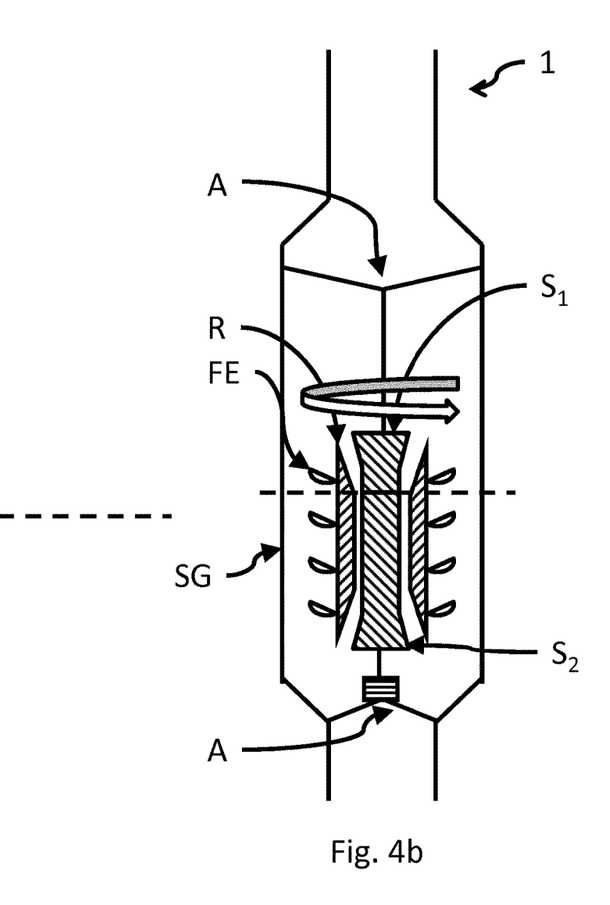
FIG. 4b shows an axial, sectional representation of an exemplary schematic arrangement of another embodiment of an inventive pump according to FIG. 4a in a second state.

FIGS. 4a and 4b show an axial cross section of another exemplary design in a first state, which is shown in FIG. 4a, for placement in the application site and in a second state, which is shown in FIG. 4b, ready for operation at the application site. A radial cross section yields similar views, so a corresponding description will be omitted here.

A pump 1 for implantation into a vessel or a heart is then introduced into the cardiovascular system of the body at an appropriate place. In this process, the pump 1 is in a first state, which is shown in FIG. 4a, in order to then be able to be functionally changed over to a second state in the vessel or in the heart.

For the purpose of being transported to the application site, the pump 1 is mounted in its first state on a wire guide of a suitable catheter, for example, or pushed via a guide wire. Alternatively, the transport can also occur via a catheter or a sheath without a guide wire. The pump 1 itself has a drive part and a delivery part FE. In the first state (FIG. 4a), the drive part is not yet functional. The drive part only becomes functional as a result of being changed over to the second state. In the embodiment of FIGS. 4a and 4b, the delivery part FE is mounted on the rotor R, for example.

The drive part has an electric motor, which is embodied as a wet rotor, for example. Wet rotors are especially advantageous, since they enable a comparably good flow rate while also not having any problems with respect to the fact that the motor must be specially encapsulated in order to prevent the motor from becoming gummed up or blocked or corroded by blood or components thereof and not posing a danger for the blood circulation by exchanging lubricants with the blood.

As a rule, the rotor R of the electric motor is arranged separately from the stator S of the electric motor for the transport.

In FIG. 4a, the stator S is divided into two portions $S_1$ and $S_2$, for example, and the rotor R is arranged initially in the first state therebetween, i.e., on different planes, and the motor is not operable. The rotor R only becomes rotatable through the positioning of the stator S in the rotor R and can then cause the delivery part FE to rotate (FIG. 4b). In the process, the two stator portions $S_1$ and $S_2$ are moved spatially closer together. Alternatively, during the change from the first state to the second state, it is also possible for the stator S (or a portion thereof $S_1/S_2$) to be introduced into the rotor R from only one side.

The rotor R and stator S of the electric motor engage in one another only upon changing over into the second state at the application site. Different techniques can be used for this purpose. Exemplary techniques include pulling or pushing by means of a guide wire on a catheter, shape memory alloys, spring forces, etc. For instance, the pump can be biased in the first state in the manner of a spring, and upon release (of a locking mechanism), the stored force is released and results in an expansion or to the assembly of the individual parts. As in FIG. 1b in comparison to FIG. 1a, an outer supporting structure SG can be deployed in the process and the corresponding vessel or myocardium MYO optionally widened. Besides widening the lumen in order to make pump output available, this expansion can also assume the function of supporting the pump 1 in the vessel or in the myocardium MYO.

In the second state, which occurs at the application site, the rotor R can then drive the delivery part FE. The state is shown in FIG. 4b.

In order to change over from the first to the second state, a shaft can be provided which can be shortened, for example. For instance, this change can occur as a result of the fastener A in FIGS. 4a and 4b changing its alignment relative to the shaft and relative to the supporting structure SG.

In an especially simple embodiment, a provision is additionally made that the drive shaft W and the rotor R are integrally formed. This enables production costs to be saved and sources of errors to be minimized. On the other hand, the rotor R and the drive shaft W can also be embodied in multiple parts, thereby enabling greater flexibility during transport, for example. In this way, introduction through already highly calcified vessels is simplified substantially, for example, since more flexible pumps 1 can thus be transported that are assembled only upon use.

In an alternative embodiment, the rotor can also be broken down into two or more parts in the first state that are, in turn, joined together only upon changing over into the second state.

Without limiting its generality, the invention permits the use of different bearings. For example, mechanical bearings can be used. In this case, wear-resistant materials are especially advantageously used for the bearing itself or for coatings of individual parts of the bearing. Exemplary materials have ceramic or stainless steels. Particularly, however, a magnetic bearing or a magnetomechanical bearing or a magneto-hydromechanical bearing of the drive shaft W and of the rotor R is supported. Magnetic bearings in particular prove advantageous, since the friction can be minimized in them, and the use thereof in conjunction with wet rotors is especially advantageous. In particular, the magnetic bearing (as well as the magnetically supported magnetomechanical or magneto-hydromechanical bearing) enables the cross section available for the throughput to be enlarged and for wear to be minimized. This has an advantageous impact on the delivery rate and/or on the energy consumption. For example, an axial magnetic bearing can be made available especially simply with the arrangement from FIGS. 4a and 4b, whereas radial magnetic bearings can be produced with particular ease with the arrangements from FIGS. 2 and 3. Since the figures can only illustrate principles, mixed forms of radial and axial bearings can also be implemented.

In order to enable the introduction of the pump 1 according to the invention and the changeover from the first state to the second state, a provision can be made, for example, that the change of state is brought about by heat input and/or an applied mechanical force and/or an external magnetic field and/or an internal magnetic field. Heat input can be achieved, for example, through the external coupling of an eddy current, an internally introduced heat source and/or a combination of the two. Direct heating of (portions of) the pump 1 or indirect heat transfer to (portions of) the pump 1 can be provided. It is advantageous to heat only the portions that also enable a heat-induced state change to occur. There is also the possibility of having the heat input occur through the body temperature. The cooling of (at least portions of) the pump 1 prior to implantation may be necessary for this purpose. Alternatively or in addition, a mechanical force can be used that is applied by means of a guide wire or one or more other manipulation wires such as those used in catheters.

In particular, it is advantageous if the delivery part FE and/or the rotor R and/or the stator S and/or an external supporting structure SG have a shape memory alloy or a self-expansion capability. These materials enable a structure that is especially simple to produce and can be changed from the first state to another state through heating or cooling, for example. In addition, these materials have already been tested as vascular supports and have good biocompatibility.

In advantageous embodiments, the pump 1 has a fixing means for fixation in the heart (e.g., cardiac muscle/myocardium) and/or the vessel. Exemplary embodiments can be embodied in the manner of anchors or anchor hooks or rivet heads. This ensures secure anchoring in the vessel or in the heart. Alternatively, the pump 1 can also be fastened to the myocardium using an annular structure, for example using appropriate (surgical) suture material or glue. Without limiting the generality, several different fixing means can also be provided.

In order to provide a further reduction of the cross section in the first state, a provision can also be made that the stator S is also compressed in a first state and is expanded as a result of the changeover to the second state.

Also in order to provide a further reduction of the cross section in the first state, a provision can also be made that the delivery part FE is not functional in a first state and becomes functional as a result of the changeover to the second state. For example, the delivery means FE or parts thereof can have a shape memory alloy that brings about the deployment of the delivery means only upon activation (or after activation) of the second state.

Figure 7:
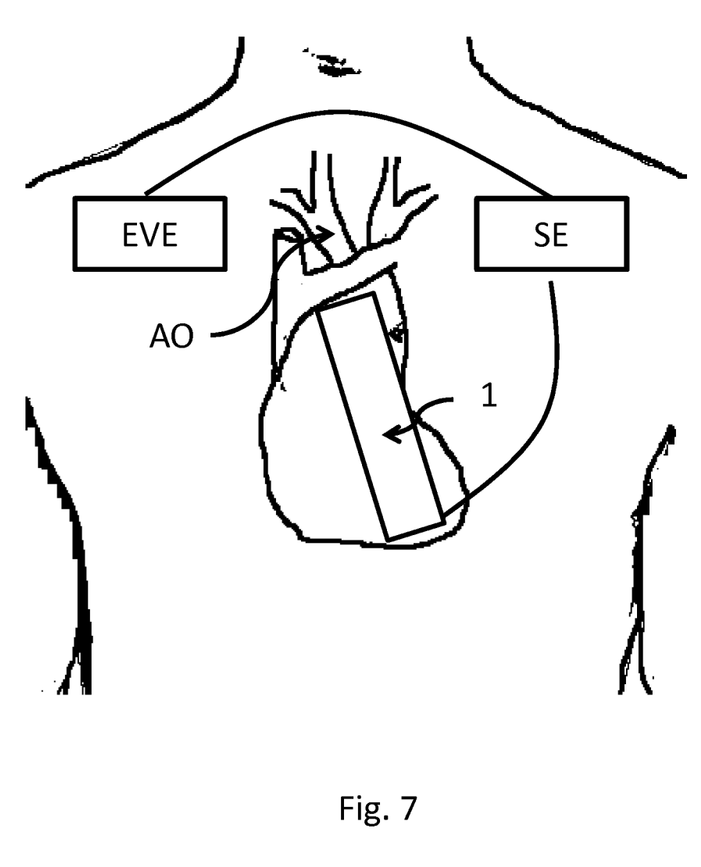
FIG. 7 shows an exemplary arrangement of units of an inventive pump in relation to a human body.

As shown in FIG. 7, a power supply unit EVE can be associated with the pump 1.

In advantageous embodiments, the power supply unit EVE is charged through induction. In this way, problems with infections through connecting wires that are introduced into the body are avoided, and an intracorporeal arrangement is made possible.

Inductive charging contributes to the patient's comfort, since it is now possible to charge the power supply unit without great effort, e.g., in resting periods, without the nuisance of cables.

Moreover, an intracorporeal power supply unit EVE is advantageous in that a patient equipped with it enjoys greater freedom and does not have to constantly keep the connecting cables in consideration. Nevertheless—without limiting the generality—a provision can also be made that the power supply unit EVE is disposed extracorporeally. This can be advantageous, for example, if the power supply unit EVE is too large in comparison to the available space. Such a case can arise, for example, if the pump 1 is implanted in children and youths or if the energy demand is so great that the necessary battery capacity for expedient operation would result in an excessively large and/or heavy power supply unit EVE. Without limiting the generality, the power supply unit EVE can also be embodied in several sub-units (even distributed in different locations).

Especially advantageously, this power supply unit EVE and the pump 1 can be implanted in a minimally invasive manner.

In embodiments of the invention, a control unit SE can also be associated with the pump 1 that supports an existing volume flow depending on a volume to be delivered.

Without limiting the generality, the control unit SE can be arranged extracorporeally or intracorporeally. An intracorporeal control unit SE is especially advantageous, however, since it minimizes the risk of infections. Moreover, an intracorporeal control unit SE is advantageous in that a patient equipped with it enjoys greater freedom and does not have to constantly keep the connecting cables in consideration.

Alternatively or in addition, a provision can also be made for the pump 1 to be controlled manually and/or automatically. With a manual control, for example, it is possible for the patient to adjust the pump output appropriately as soon as he notices or knows that he has or will have greater pumping demand. It can also be used by relevant medical staff, for example. The manual control can be embodied in any of several ways. For example, a mechanical control can be provided by means of (pressure) switches arranged under the skin so as to be palpable and switchable. Alternatively or in addition, a radio control or another electromagnetically coupled control can be provided.

The automatic control can be designed in various ways. For example, a time-controlled control can take the daily routine into account, with less or even no support being made available during periods of rest, for example. In other examples, the automatic control can also have a hemodynamic control. For example, the blood flow can be detected by a suitable device, and when high blood flow is demanded appropriate support can be made available. Suitable parameters for detecting the blood flow can be derived from cardiac output, pulse and/or blood pressure, for example. This can be made available in a pulse-controlled manner, for example, or—alternatively or in addition—in a blood pressure-controlled manner, or—alternatively or in addition— via the pump 1 itself, which can act as a throughput meter in the off state, for example. Moreover, the automatic control can also be achieved by means of motion control. If a certain measure of movement is detected by means of motion sensors, such as those known from smartphones, navigation devices or the like, then appropriate support is activated. Mixed forms of the automatic controls described above can also readily be used.

This makes it possible to activate the pump 1 only when a commensurately elevated cardiac output is needed. This ability to be activated on an as-needed basis makes it possible to minimize energy consumption, thereby enabling an advantageous design with intracorporeal control unit SE and/or intracorporeal power supply unit EVE, which represents a substantial improvement in patients' quality of life.

The control unit SE and the power supply unit EVE can also readily be embodied as an integrated unit; that is, insofar as the units were portrayed as separate in the foregoing, this separation need not necessarily be understood as physical, but rather serves merely to illustrate the different tasks.

Figure 5A:
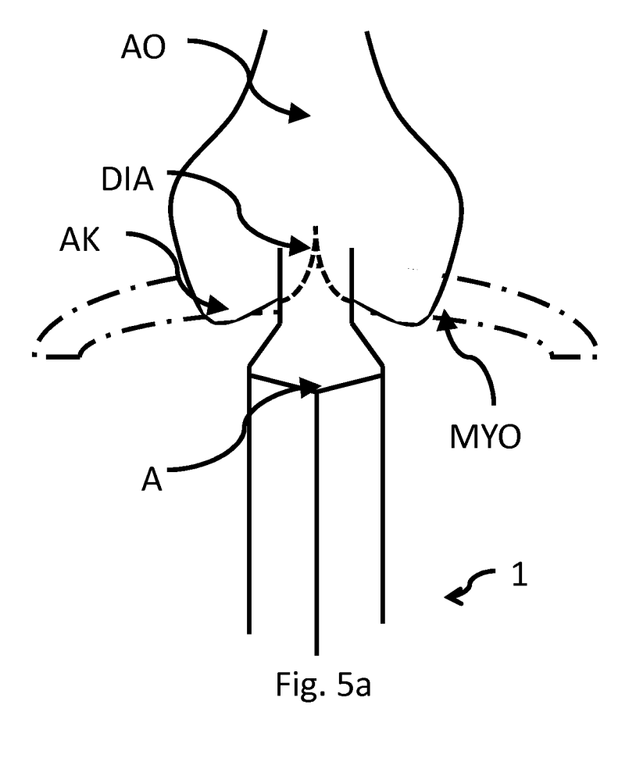
FIG. 5a shows an axial, sectional representation of an exemplary schematic arrangement concerning an aspect in a first (closed) state.
Figure 5B:
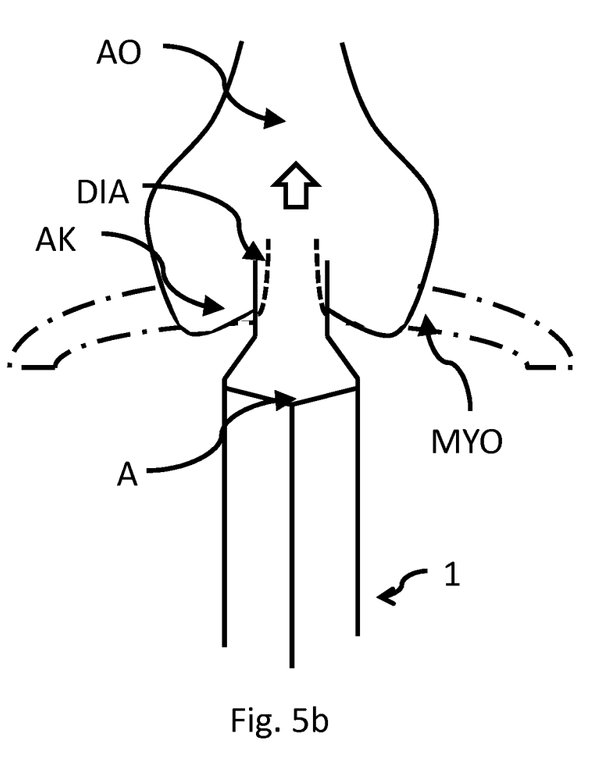
FIG. 5b shows an axial, sectional representation of an exemplary schematic arrangement according to FIG. 6a concerning an aspect in a second (open) state.
Figure 6A:
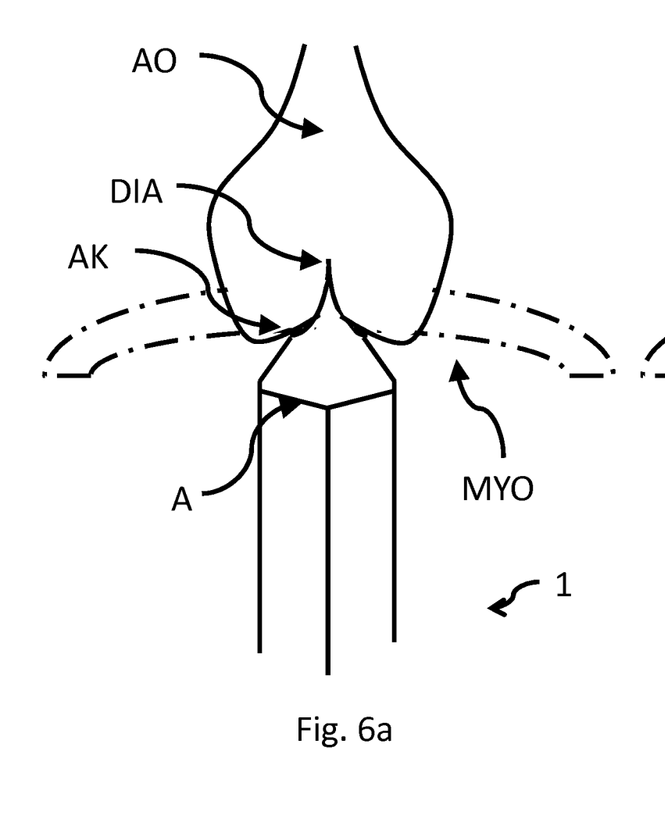
FIG. 6a shows an axial, sectional representation of an exemplary schematic arrangement concerning an aspect in another embodiment in a first (closed) state.
Figure 6B:
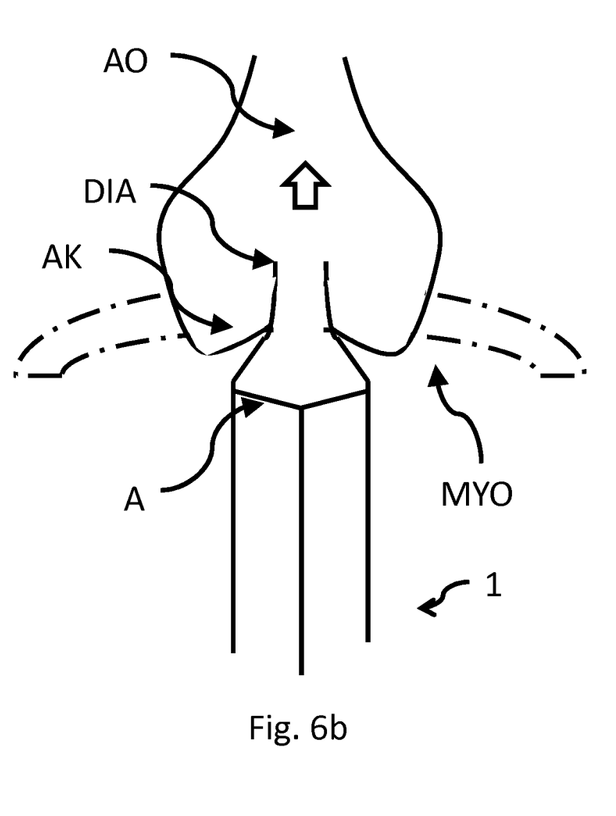
FIG. 6b shows an axial, sectional representation of an exemplary schematic arrangement according to FIG. 6a concerning an aspect in another embodiment in a second (open) state.

What is more, an appropriate design prevents retrograde flow. This is prevented, for example, by a diaphragm DIA such as that shown in FIGS. 5a and 5b as well as 6a and 6b. These illustrated design variants do not constitute any limitation, and other embodiments for preventing backflow, such as appropriately shaped non-return valves, are also included. In FIGS. 5a and 5b—which show, for the sake of example, a device for preventing backflow—a diaphragm represented by a broken line is integrated or built into the pump 1, with the outflow tract of the pump 1 being arranged over the aortic valve and into the ascending aorta AO. Alternatively, a biological or mechanical valve can be introduced here which restricts or prevents backflow. In FIGS. 5a and 5b, the end of the pump is embodied in the manner of a diaphragm. FIGS. 5a and 6a each show a case in which a retrograde flow through the pump 1 is prevented, whereas FIGS. 5b and 6b each show a case in which antegrade flow from the pump is enabled.

In addition, through the general positioning of the pump 1 in the bloodstream, thrombus formation on the pump 1 itself is prevented or reduced even in the off state.

The delivery part FE can also be embodied in various ways. As a rule, however, the delivery part FE will, at least in portions, have a screw shape or a propeller shape. Without limiting generality, the delivery part FE can also be magnetically coupled with the rotor R and/or the drive shaft W.

By virtue of its design, the present invention enables introduction using minimally invasive techniques. Through the provision of a drive part to be put in operation at the application site, its radial cross section is reduced and transport is facilitated such that it can be moved to the application site using the minimally invasive techniques. An apical, atrial or transvascular access can be used, for example.

Without limiting generality, other components of the pump 1 can also be the object of expandable means. For example, the delivery part as well as other components can become operable only at the application site, for example by virtue of being expanded during the expansion of the drive part or separately therefrom. To this end, different techniques or several techniques can be used simultaneously or in a certain temporal succession for different elements of the pump 1 according to the invention. Exemplary techniques include pulling or pushing by means of a guide wire on a catheter, shape memory alloys, spring forces, etc.

Insofar as reference is made in the foregoing to specific organs, such as the heart or cardiac muscle (myocardium), this is merely for the sake of example. In principle, the device is suitable for any lumen in the human or animal body.

By virtue of the invention, it is particularly possible to make inventive pumps available that can be introduced into the body by means of a 32 French catheter (or smaller), particularly a 24 French catheter or smaller. A minimally invasive application can thus be readily achieved, thus enabling even those patients to be treated who otherwise could not be treated due to the high risk associated with an operation. What is more, it is now possible to treat patients in whom, due to the sizes of previous pumps or delivery systems, the use of pumps was either not possible or only possible to a limited extent (e.g., in pediatrics, neonatology, or in patients with multiple morbidities).

What is claimed is:

1. A pump for implantation into a blood vessel or a heart, with the pump being introduced in a first state into the blood vessel or heart in order to then be functionally changed over to a second state in the blood vessel or in the heart, the pump comprising:
   a drive part; and
   a delivery part,
   wherein the drive part is not functional in the first state and becomes functional as a result of the changeover to the second state,
   wherein the drive part has an electric motor,
   wherein the electric motor is embodied as a wet rotor, and
   wherein, in the first state, the wet rotor of the electric motor and a stator of the electric motor are arranged in the pump so as to be spaced apart from one another in a longitudinal direction of the pump, so that a rotation of the wet rotor by the stator is not possible, and
   wherein, in the second state, the wet rotor of the electric motor is moved in the longitudinal direction into the stator of the electric motor while the pump is situated in the blood vessel or heart, wherein the wet rotor can drive the delivery part in the second state, wherein the delivery part has a drive shaft that enables rotational movement of the delivery part with respect to the drive shaft.

2. The pump as set forth in claim 1, wherein the drive shaft and the wet rotor are integrally formed.

3. The pump as set forth in claim 2, wherein the drive shaft is designed as a shaft that shortens upon the changeover from the first state to the second state, enabling the wet rotor to be introduced into the stator.

4. The pump as set forth in claim 2, wherein the drive shaft is supported magnetically or mechanically or magnetomechanically or magnetohydromechanically.

5. The pump as set forth in claim 1, wherein the wet rotor is supported magnetically or mechanically or magnetomechanically or magnetohydromechanically.

6. The pump as set forth in claim 1, wherein the state change is brought about by a heat input and/or an applied mechanical force and/or an external magnetic field and/or an internal magnetic field and/or self-expansion.

7. The pump as set forth in claim 1, wherein the delivery part and/or the wet rotor and/or the stator and/or an external supporting structure has a shape memory alloy.

8. The pump as set forth in claim 1, wherein the pump has a fixing means for fixation in the heart and/or the blood vessel.

9. The pump as set forth in claim 1, wherein the stator is compressed in the first state and expanded as a result of the changeover to the second state.

10. The pump as set forth in claim 1, wherein the delivery part is not functional in the first state and becomes functional as a result of the changeover to the second state.

11. The pump as set forth in claim 1, wherein a power supply unit is associated with the pump.

12. The pump as set forth in claim 11, wherein the power supply unit can be charged through induction.

13. The pump as set forth in claim 11, wherein the power supply unit is arranged extracorporeally or intracorporeally.

14. The pump as set forth in claim 1, wherein a control unit is associated with the pump that supports an existing volume flow depending on a volume to be delivered.

15. The pump as set forth in claim 14, wherein the control unit is arranged extracorporeally or intracorporeally.

16. The pump as set forth in claim 14, wherein the pump can be controlled manual and/or automatically.

17. The pump as set forth in claim 16, wherein, in the case of automatic control, the control system is selected from a group including time-controlled, hemodynamic control, and motion control.

18. The pump as set forth in claim 1, wherein the delivery part has a screw shape or a propeller shape at least in portions.

19. The pump as set forth in claim 1, at least a portion of the pump has a coating for reducing friction, adhesion, and deposits.

20. The pump as set forth in claim 1, wherein the pump has a device for preventing backflow.

21. The pump as set forth in claim 1, wherein the pump has a diameter which is such that it can be passed through a catheter having a diameter of French 32 or less.

* * * * *